United States Patent
Hunter

(10) Patent No.: US 6,291,838 B1
(45) Date of Patent: Sep. 18, 2001

(54) GAS SENSING DIODE COMPRISING SIC

(75) Inventor: Gary William Hunter, Avon, OH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/448,406

(22) Filed: Nov. 15, 1999

Related U.S. Application Data

(62) Division of application No. 09/093,840, filed on May 29, 1998, now Pat. No. 6,027,954.

(51) Int. Cl.$^7$ ................................................ H01L 31/0312
(52) U.S. Cl. .............................. 257/76; 257/77; 257/252; 257/253; 257/414; 257/473; 438/48; 438/49
(58) Field of Search ............................... 257/76, 77, 473, 257/414, 252, 253; 438/48, 49

(56) References Cited

U.S. PATENT DOCUMENTS

| | | | |
|---|---|---|---|
| 3,597,270 | 8/1971 | Scott-Monck et al. | 117/217 |
| 3,645,785 | 2/1972 | Hentzschel | 117/217 |
| 3,660,154 | 5/1972 | Scott-Monck et al. | 117/200 |
| 4,622,736 | 11/1986 | Drobny | 29/571 |
| 5,270,252 | 12/1993 | Papanicolaou | 437/176 |
| 5,362,975 * | 11/1994 | von Windheim et al. | 257/76 |
| 5,399,883 | 3/1995 | Baliga | 257/57 |
| 5,442,200 * | 8/1995 | Tischler | 257/77 |
| 5,612,232 | 3/1997 | Thero et al. | 437/39 |
| 5,635,412 * | 6/1997 | Baliga et al. | 438/520 |
| 5,656,827 * | 8/1997 | Kang et al. | 257/76 |
| 5,929,523 * | 7/1999 | Parsons | 257/750 |
| 6,027,954 * | 2/2000 | Hunter | 438/49 |
| 6,109,094 * | 8/2000 | Baranzahi et al. | 73/31.06 |

OTHER PUBLICATIONS

Tobias et al. "Fast Chemical Sensing with Metal Insulator Silicon Carbide Structures" IEE Elector Device Letters, vol. 18; p. 287–289 (Jun. 6, 1997).

Karlstein, et al. "Electrical Properties of MIS Structures on 6N–Sic". Linkoping University, Conference. Pg. X–17 to X–22. (Jun. 5–10, 1994).

\* cited by examiner

*Primary Examiner*—William Mintel
(74) *Attorney, Agent, or Firm*—Kent N. Stone

(57) ABSTRACT

A diode for sensing hydrogen and hydrocarbons and the process for manufacturing the diode are disclosed. The diode is a Schottky diode which has a palladium chrome contact on the C-face of an n-type 6H Silicon carbide epilayer. The epilayer is grown on the C-face of a 6H silicon carbide substrate. The diode is capable of measuring low concentrations of hydrogen and hydrocarbons at high temperatures, for example, 800° C. The diode is both sensitive and stable at elevated temperatures.

15 Claims, 2 Drawing Sheets

DEPOSITING AN n-TYPE 6H SiC EPILAYER ON A C-FACED 6H SiC SUBSTRATE

ETCHING THE EPILAYER

RINSING THE EPILAYER WITH DEIONIZED WATER

BLOW DRYING THE EPILAYER WITH N2 GAS

DEPOSITING A $Pd_{.9}Cr_{.1}$ CONTACT ON THE EPILAYER

DEPOSITING AN ALUMINUM BACKSIDE CONTACT ON THE 6H SiC SUBSTRATE

FIG. 2

GAS SENSING DIODE COMPRISING SIC

This application is a divisional of Ser. No. 09/093,840, now issued as U.S. Pat. No. 6,027,954, which was filed on May 29, 1998.

FIELD OF THE INVENTION

The instant invention is a Schotky diode. Its principal use is the measurement of hydrogen and hydrocarbons occurring at low concentrations and high temperatures.

ORIGIN OF THE INVENTION

The invention described herein was made by an employee of the United States Government and may be manufactured and used by or for the Government for Government purposes without the payment of any royalties thereon or therefor.

BACKGROUND OF THE INVENTION

U.S. Pat. No. 5,270,252 to Papanicolaou is a Schottky diode on beta silicone carbide. The metals taught in the Papanicolaou disclosure are platinum, tungsten, titanium tungsten, gold and aluminum. The Schottky diode of the Papanicolaou disclosure is used for high temperature semiconductor applications and, in particular, it is used as a rectifying diode.

U.S. Pat. No. 5,612,232 to Thero, et al. is a Schottky diode for use in high temperature applications but it cannot be used as a gas sensor. Thero, et al. teaches the use of a silicon carbide semiconductor with nickel and tungsten as metals.

U.S. Pat. No. 4,622,736 to Drobny discloses Schottky diodes for use in connection with a silicon semiconductor. Tungsten, titanium-tungsten, and vanadium are the metals used in the invention The Drobny Schotky diode is not a gas sensor.

The development of a Schotky diode structure has been reported by the researchers at Linkoping University. The structure of the Linkoping sensor is Pt on TaSix on SiO2 on SiC. The Pt/TaSix/SiO2 thicknesses are 100 nm/10 nm/5 nm respectively. The sensor responses are stable and fast but they are not highly sensitive.

SUMMARY OF THE INVENTION

The instant invention discloses a Schottky diode which includes an alpha silicon carbide substrate, an alpha silicon carbide epilayer, a backside contact, and a palladium chrome contact. The silicon carbide epilayer is an n-type carrier as is the silicon carbide substrate. The epilayer is grown on a commercially available n-type 3.5° off-axis polished c-FACE 6H-SiC substrate. The epilayer surface was etched by a dilute hydrofloric solution, rinsed with deionized water and blown dry with nitrogen prior to the deposition of the palladium chrome film thereon. Approximately 400 Angstroms of the palladium chrome alloy are magnetron sputter deposited onto the C-face of the epilayer to form a palladium chrome/silicon carbide diode. The ratio of the palladium to chrome is controlled during the deposition thereof.

In the preferred embodiment the palladium chrome deposition is 90 atomic percent palladium and 10 atomic percent chrome. A backside substrate contact is formed by sputtering aluminum thereon.

The palladium chrome contact surface is a catalytic material in the presence of hydrogen. The presence of hydrogen results in an increased current flow through the diode with a given bias voltage applied to the diode. Hydrogen dissociates when it reacts with the palladium chrome.

It is an object of the invention to provide a sensor which is stable and sensitive at high temperatures of 425° C. and above.

It is a further object of the present invention to provide a palladium chrome contact on an alpha 6H silicon carbide substrate with a metal backside contact.

It is an object of the present invention to provide a gas sensor using an alloy on the C-face of a silicon carbide epilayer on a silicon carbide substrate.

It is an object of the present invention to provide a sensor which is stable and sensitive following exposure to high temperatures for long periods of time.

It is an object to provide a Schottky diode employing silicon carbide as the semiconductor to detect hydrogen and hydrocarbons at low concentrations.

It is an object to provide a hydrogen and/or hydrocarbon sensor which can be used at elevated temperatures for prolonged periods of time for use in catalytic combustion control systems or other applications which depend on the presence of hydrogen or hydrocarbons.

BRIEF DESCRIPTION OF THE DRAWINGS

Drawing

Figure 1:
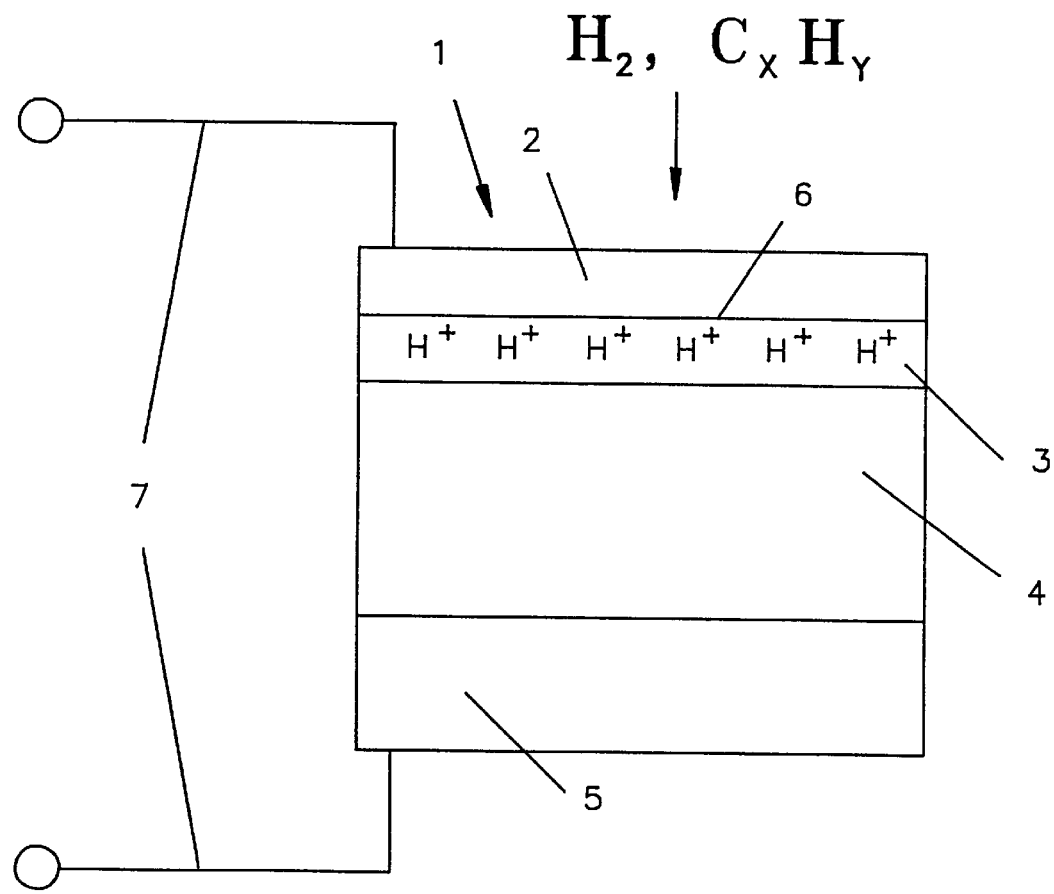
FIG. 1 illustrates the $Pd_{0.9}Cr_{0.1}$ contact on the C-face of an α Silicon Carbide epilayer on the C-face of the α Silicon Carbide substrate. A backside metal contact is also shown.

Drawing FIG. 2 schematically illustrates the process for manufacturing the Schottky diode.

DETAILED DESCRIPTION OF THE INVENTION

A Schottky diode is formed by the junction of a metal and a semiconductor. Other diodes are formed by the junction of a p-type and an n-type semiconductor.

FIG. 1 is a schematic representation of the structure of the invention. FIG. 2 is a schematic of the process used (described above) to manufacture the instant invention. The advantage of the Schottky diode 1 of the present invention is that a large signal difference is obtained in response to a corresponding small concentration of hydrogen or hydrocarbons in high temperature applications. The Schottky diode of the present invention has a high gain. In other words, the Schottky diode 1 used as a high temperature sensor of hydrogen and hydrocarbons is sensitive and stable. Referring to FIG. 1, the Schotky diode of the present invention uses an α silicon carbide (SiC) substrate 4 and an α silicon carbide (SiC) epilayer 3.

Epilayer 3 is 4–5 μm thick and is grown or deposited on the silicon carbide (SiC) substrate 4 by chemical vapor deposition. Silicon carbide is used because it has superior thermal properties and does not degrade at temperatures as high as 800° C. Epilayer 3 and substrate 4 are both n-type α SiC. Substrate 4 is commercially available 3.5° off-axis polished C-face 6H-SiC.

The epilayer 3 is a n-type C-faced 6H-SiC. Reference numeral 6 indicates the C-face of the epilayer 3. Once deposited on the substrate, the epilayer 3 is etched with hydrofloric acid and is then rinsed with deionized water. These procedures are to chemically clean the SiC surface. Next, the epilayer is blown dry with gaseous nitrogen ($N_2$). Some slight oxidation of the surface of the epilayer may occur in this process without any degradation of the Schotuy diode for use as a sensor of hydrogen and hydrocarbons.

When dried, the C-face of the epilayer has an alloy 2 deposited thereon. In the preferred embodiment the alloy 2 is palladium chrome (PdCr). The palladium chrome alloy is deposited onto the C-face of the epilayer using magnetron sputtering. Approximately 400 Angstroms of palladium chrome are used in the preferred embodiment. However, 300–1000 Angstroms of an alloy such as palladium chrome may be used. Other forms of physical deposition can be used as well such as evaporation. Chemical vapor deposition may also be used. The ratio of palladium is 90 atomic percent to 10 atomic percent chrome. This ratio may vary from about 70 to 95 atomic percent palladium to 5 to 30 atomic percent chrome. Palladium dissociates hydrogen. A backside metallic contact 5 is affixed to the SiC substrate 4 by magnetron sputtering. In the preferred embodiment the contact 5 is aluminum.

The thermal stability of the Schottky diode of the preferred embodiment, to wit, $Pd_{0.9}Cr_{0.1}$/6H-SiC, is improved compared to a Pd/SiC diode. Further, the response of a $Pd_{0.9}Cr_{0.1}$/6H-SiC diode to hydrogen is stable after long heating periods.

Reference numeral 7 indicates the sensor electrical connections. A bias voltage is applied to the Schottky diode 1 (i.e., the sensor) in operation and the presence of hydrogen or hydrocarbons causes a change in the current measured in the circuit The foregoing description of the invention has been set forth by way of example only and in no way limits the scope of the invention. The scope of the invention is set forth in the attached claims.

What is claimed is:

1. A gas sensing diode comprising:
   a silicon carbide substrate;
   a silicon carbide epilayer;
   a backside contact; and,
   a palladium chrome contact, located on said silicon carbide substrate.

2. A gas sensing diode as claimed in claim 1 wherein said silicon carbide epilayer is an n-type alpha silicon carbide carrier.

3. A gas sensing diode as claimed in claim 1 wherein said silicon carbide substrate is an n-type alpha silicon carbide carrier.

4. A gas sensing diode as claimed in claim 2 wherein said silicon carbide epilayer is a 6H silicon carbide epilayer.

5. A gas sensing diode as claimed in claim 3 wherein said silicon carbide substrate is a 6H silicon carbide substrate.

6. A gas sensing diode as claimed in claim 5 wherein said 6H silicon carbide substrate includes a 3.5° off-axis polished C-face.

7. A gas sensing diode as claimed in claim 1 wherein said palladium chrome contact is approximately 400 Angstroms thick.

8. A gas sensing diode as claimed in claim 5 wherein said backside contact is aluminum.

9. A gas sensing diode as claimed in claim 7 wherein said palladium is approximately 90 atomic percent of said palladium chrome contact.

10. A diode comprising:
    an n-type 6H silicon carbide substrate;
    an n-type 6H silicon carbide epilayer;
    a backside contact; and,
    a precious metal alloy contact, located on said silicon carbide substrate.

11. A diode as claimed in claim 10 wherein said precious metal alloy contact is 90 atomic percent palladium and 10 atomic percent chrome.

12. A diode as claimed in claim 10 wherein said 6H silicon carbide substrate includes a polished C-face.

13. A diode as claimed in claim 12 wherein said epilayer is affixed to said polished C-face of said substrate.

14. A diode as claimed in claim 10 wherein said epilayer includes a C-face and said palladium chrome contact is affixed to said C-face of said epilayer.

15. A diode as claimed in claim 10 wherein said precious metal alloy is about 70 to 95 atomic percent palladium and 5 to 30 atomic percent chrome.

* * * * *